United States Patent [19]

Patton, Sr. et al.

[11] Patent Number: 4,698,850
[45] Date of Patent: Oct. 13, 1987

[54] THERAPEUTIC EXERCISE GLOVE

[76] Inventors: Edward E. Patton, Sr.; Edward E. Patton, Jr., both of 5080 Fremont Ave., Jacksonville, Fla. 32210

[21] Appl. No.: 915,692

[22] Filed: Oct. 6, 1986

[51] Int. Cl.$^4$ .......................... A61F 5/10; A41D 19/00
[52] U.S. Cl. ........................................ 2/159; 2/161 A; 2/DIG. 6; 128/77
[58] Field of Search ............... 2/158, 159, 160, 161 R, 2/161 A, DIG. 6; 128/77

[56] References Cited

U.S. PATENT DOCUMENTS

| | | | |
|---|---|---|---|
| 2,083,604 | 6/1937 | Hay | 2/161 A |
| 2,751,598 | 6/1956 | Romeo | 2/161 A |
| 3,348,238 | 10/1967 | Hydock | 2/161 A |
| 3,408,657 | 11/1968 | Gallagher | 2/161 A |
| 3,880,426 | 4/1975 | Morse | 2/161 A |
| 3,918,097 | 11/1975 | Mlodoch | 2/161 A |
| 4,047,250 | 9/1977 | Norman | 2/161 A |
| 4,332,382 | 6/1982 | Smith | 2/161 A |
| 4,400,831 | 8/1983 | Rietz | 2/161 A |
| 4,447,912 | 5/1984 | Morrow | 2/159 |

Primary Examiner—Louis K. Rimrodt
Attorney, Agent, or Firm—Arthur G. Yeager

[57] ABSTRACT

A glove for use by persons taking therapeutic exercises involving use of their hands, the glove including a mitten section to enclose four fingers and a palm and wrist section to be wrapped snugly around the hand and wrist and a thumb hole to permit the thumb to extend outwardly of the glove, a plurality of adjustment straps adapted to wrap around the palm and wrist section and be fastened to the back by a "Velcro" fastener, an eye attached to the palm and wrist section, and an elongated tape attached at one end to the top of the mitten section and having a free end adapted to be threaded through the eye and doubled back upon itself to be fastened by a "Velcro" fastener so as to hold the fingers in any desired position open or closed, and another tape and eye may be provided in the palm area of the glove.

16 Claims, 12 Drawing Figures

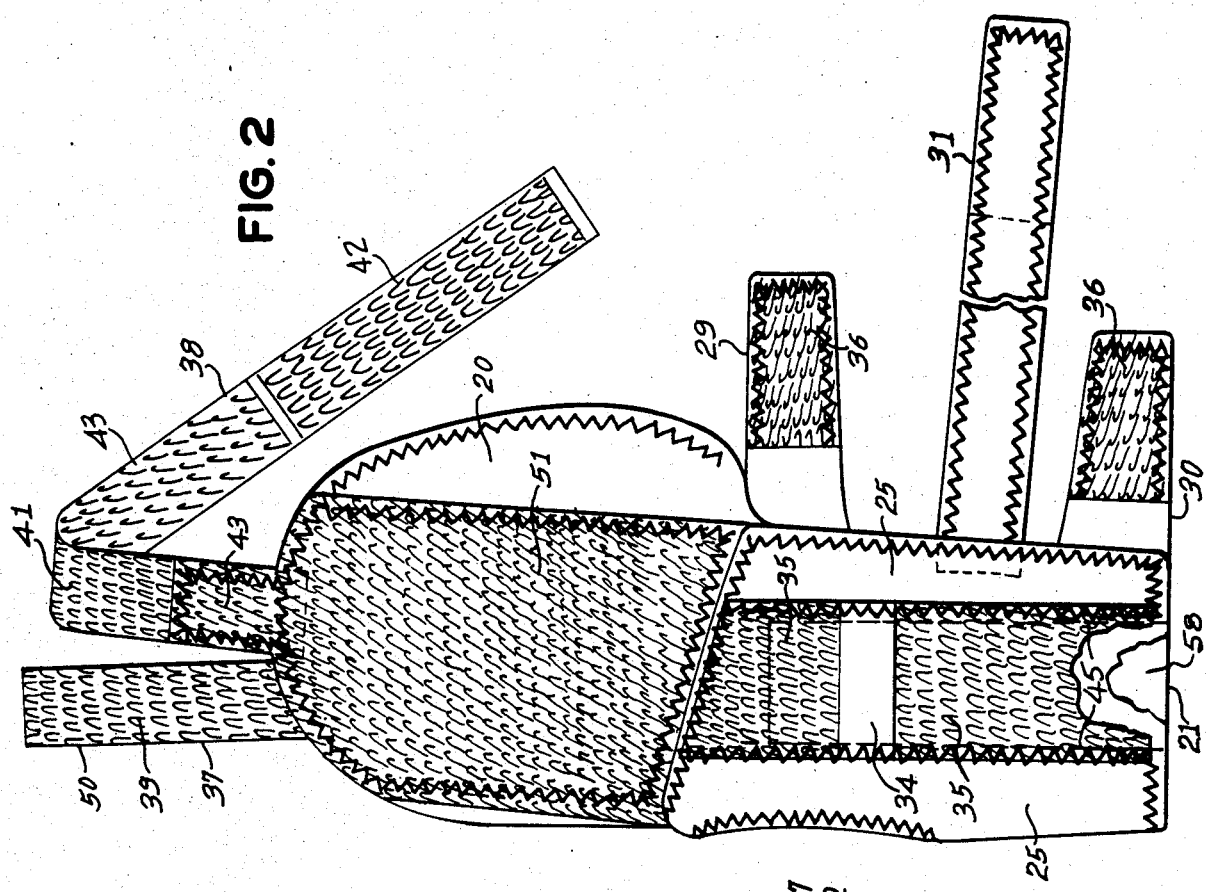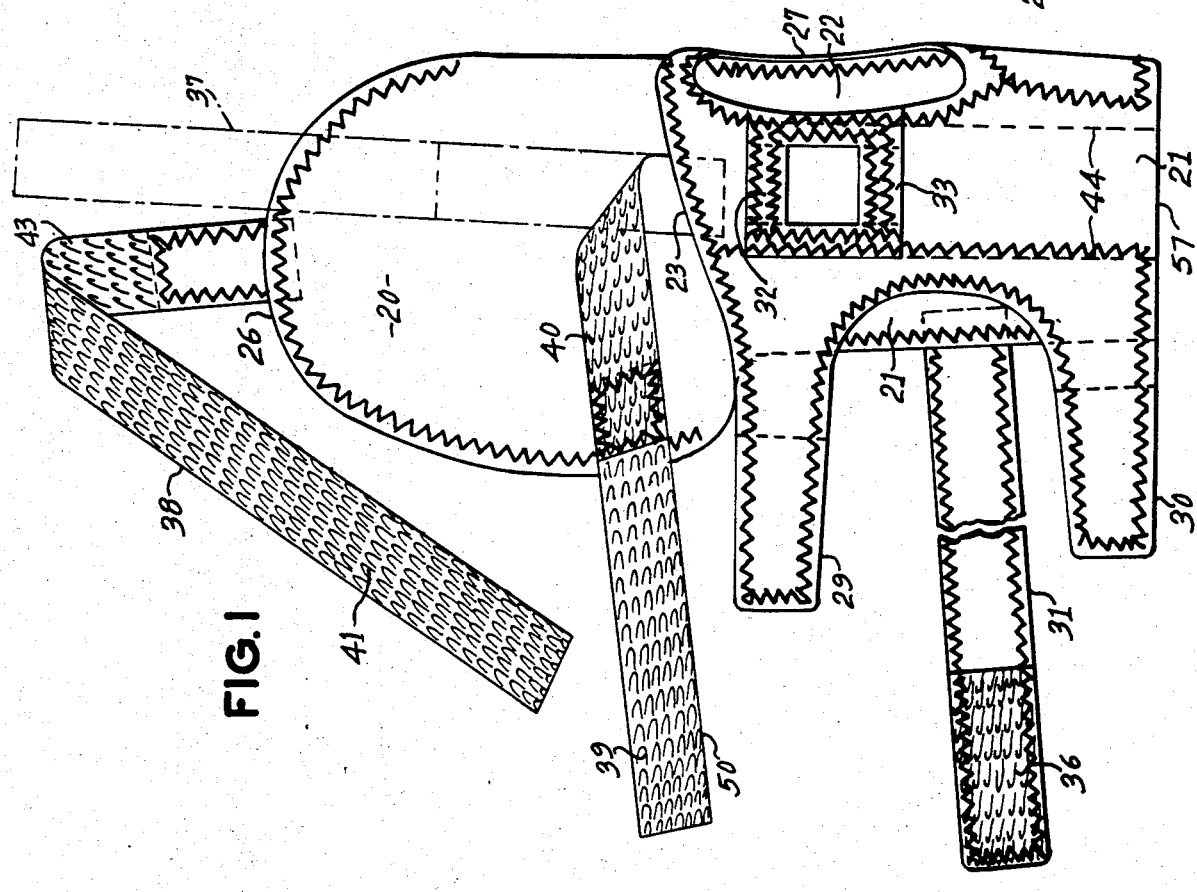

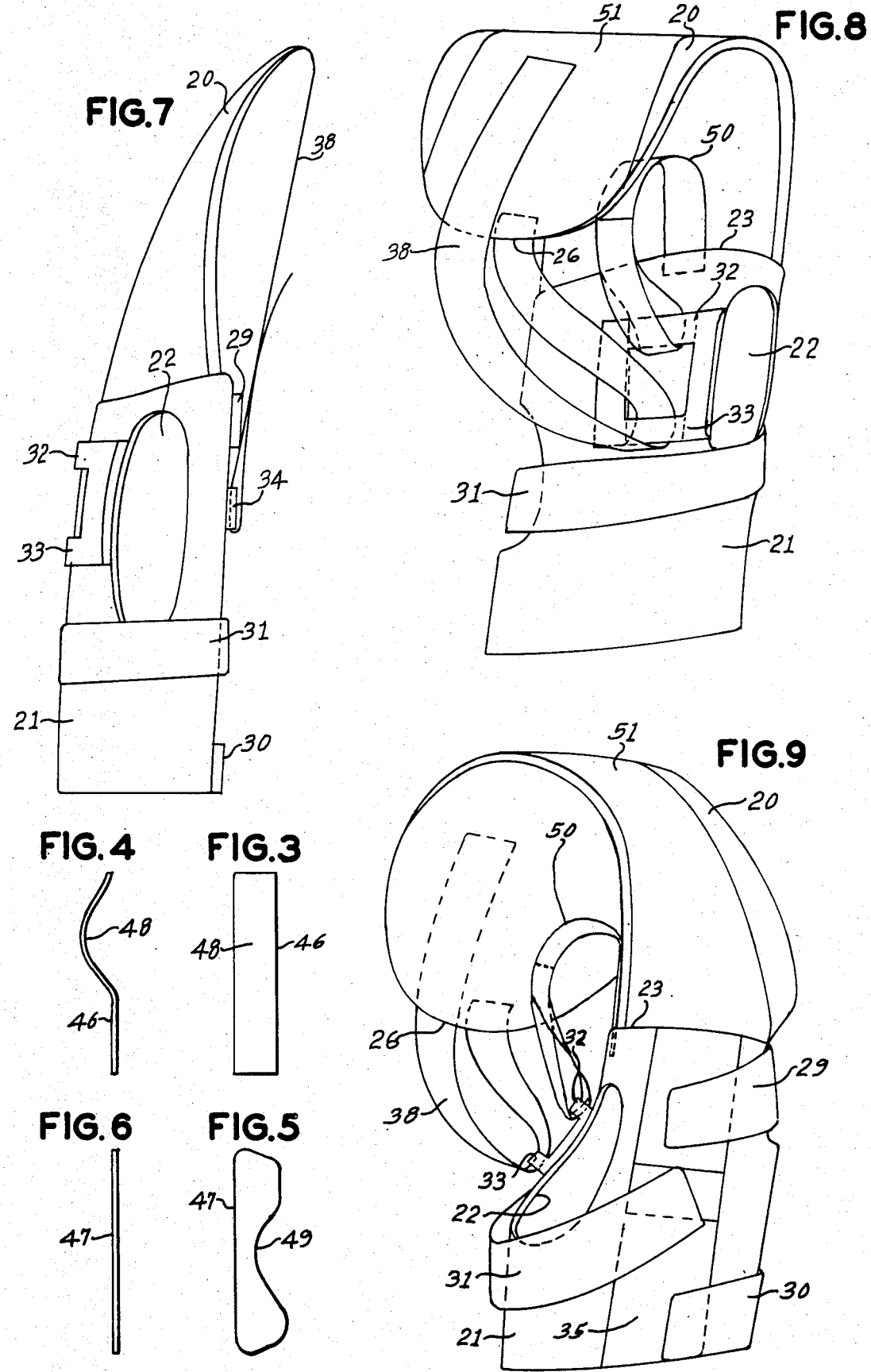

4,698,850

THERAPEUTIC EXERCISE GLOVE

BACKGROUND OF THE INVENTION

Persons handicapped by reason of a stroke, a back injury, or the like that do not have complete control of the hands and fingers are frequently unable to exercise or enjoy certain sports activities such as fishing, tennis, ping pong, golf, etc. In those instances where the handicap involves an inability to grip the handle of a fishing rod, a tennis racquet, or the like, a considerable amount of exercise and enjoyment has been lost because of the handicap.

It is an object of this invention to provide an improved glove for use by persons with impaired usage of hands. It is another object of this invention to provide a glove that can be used by handicapped persons to hold sports equipment or use exercise equipment. Still other objects will become apparent from the more detailed description which follows.

BRIEF SUMMARY OF THE INVENTION

This invention relates to a glove for use by a handicapped person during therapeutic exercise, the glove comprising a mitten section to enclose four fingers of the wearer attached to a palm and wrist section to wrap around the palm and wrist of the wearer, said palm and wrist section having a front side, a back side, and an opening for the thumb of the wearer to extend outward; the palm and wrist section adjustably tightenable to the hand and wrist of the wearer by a plurality of straps attached thereto adapted to wrap around and fasten to the back side by means of a releasable fastener employing cooperating fabric loops and fabric hooks, an elongated tape having a free end and a fixed end, said fixed end being attached to the middle of the top edge of the mitten section, a tape engaging eye attached to said palm and wrist section, the tape being adapted to be threaded through the eye and doubled back upon itself to be fastened at any selected position by means employing fabric loops and fabric hooks.

In specific embodiments of this invention there are four different types of gloves. One glove may have a single eye on the front side of the palm and wrist section and a cooperating tape affixed to the top of the mitten section. When the tape is threaded through the tunnel loop and pulled tight the fingers are closed over the palm in a loose fist. In a second glove there may be two spaced eyes, one as described above and a second eye closer to the fingers than the first one and cooperating with a second tape attached to the top of the palm and wrist section to be threaded through the second eye to hold the handle of sporting equipment tightly in the palm area while the first eye and its tape close the fingers around the handle. In a third glove, there is an eye located on the back of the palm and wrist section cooperating with a long tape attached to the top edge of the mitten section. This third glove may be used to stretch the fingers open and bend them backwards slightly so as to counteract the closed fist action found in some stroke patients. In a fourth glove there is a combination of the second and third glove, namely one having two eyes on the front side and one eye on the back side with two tapes as described for the second glove, the one elongated tape attached to the top edge of the mitten section being capable of engaging the lower eye on the front side or the eye on the back side.

BRIEF DESCRIPTION OF THE DRAWINGS

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

FIG. 1 is a front elevational view of one of the gloves of this invention opened for insertion of the hand of a wearer;

FIG. 2 is a rear elevational view of the glove of FIG. 1;

FIG. 3 is a front elevational view of a palm support which may be used in the glove of this invention;

FIG. 4 is a side elevational view of the palm support of FIG. 3;

FIG. 5 is a front elevational view of a back support which may be used in the glove of this invention;

FIG. 6 is a side elevational view of the back support of FIG. 5;

FIG. 7 is a schematic illustration of one of the embodiments of the gloves of this invention used to stretch the fingers backwards;

FIG. 8 is a schematic perspective illustration of the glove of FIGS. 1 and 2 with two front tunnel loops and cooperating tapes;

FIG. 9 is a schematic perspective illustration of the glove of FIG. 8 viewed from another angle;

DETAILED DESCRIPTION OF THE INVENTION

Figure 10:
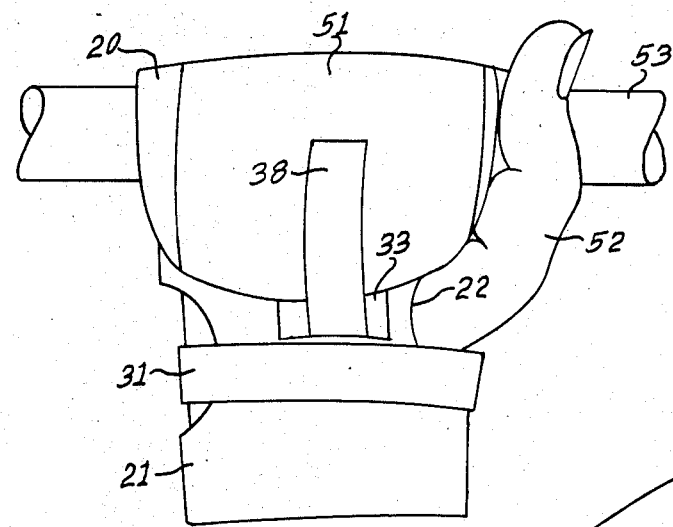
FIG. 10 is a schematic illustration of one of the embodiments of the gloves of this invention around a hand that grips a horizontal bar.

The glove of this invention may be seen in detail in FIGS. 1-6. There are four embodiments of this glove which differ in minor features as will be explained below.

The glove covers the entire hand, fingers and wrist except for the thumb. Mitten section 20 is attached to palm and wrist section 21 along juncture 23. Preferably these sections are both made of a strong flexible leather, such as pig skin or a leather-like material, such as are now available from synthetic plastic materials. Palm and wrist section 21 has a thumb hole 22 to permit the thumb of the wearer to extend outwardly of the glove and be uncovered. Mitten section 20 may be internally divided into individual finger pockets, but preferably is not so divided and comprises one large pocket enclosing all four fingers. Palm and wrist section 21 has a closed side 27 and an open side 28 in order to permit the hand and fingers to be inserted easily when putting on the glove.

Palm and wrist section 21 is capable of being snugly tightened around the palm, back of the hand, and wrist by means of straps 29, 30, and 31. In the embodiment shown here, straps 29 and 30 are both attached to the front of palm side 24 of section 21 and strap 31 is attached to the back side 25 of section 31. All straps 29, 30, and 31 wrap around and are attachable to the back side 25 of section 21 by any convenient releasable fastener means. A preferred releasable fastener means is by cooperating fabric hooks and fabric loops, known commercially as a "Velcro" fastener. In this embodiment a strip of fabric loops 35 extends vertically over the length of palm and wrist section 21, and patches of fabric hooks 36 are at the ends of each of straps 29, 30, and 31. It is to be understood that in other embodiments there may be more or less straps, other types of quick release fasteners, e.g., snaps, straps attached in some other order to palm side 24 and back side 25, a reversal of the positions of fabric hooks and fabric loops, etc. All that is necessary here is that palm and wrist section 21 be capable of being snugly tightened around the hand and wrist of the wearer by secure fasteners that are easily operated and do not interfere with the therapeutic exercise.

The features which manipulate the hand and fingers for therapeutic exercise involve tapes 37 and 38 and eyes 32, 33, and 34 which may be D-rings, but preferably are tunnel loops made of the same material as that of palm and wrist section 21. Different combinations of tapes and loops produce the four different embodiments of the glove mentioned above. The glove shown in FIGS. 1 and 2 combines all of such tapes and loops, and, therefore, is a multipurpose combination embodiment that provides all functions envisioned for therapeutic exercises. Front side 24 has two vertically spaced tunnel loops, upper loop 32 and lower loop 33. Upper loop 32 is positioned at about the middle of the palm of the wearer and lower loop is positioned at about the heel of the palm of the wearer. Both upper and lower loops 32 and 33 are generally located laterally in the middle of the front side 24. Tunnel loops 32 and 33 cooperate, respectively, with elongated tapes 37 and 38 to hold sports equipment and to hold the fingers in a gripping position. Tape 37 cooperates with tunnel loop 32 to wrap around the handle of a sports implement, such as a ping pong paddle, a tennis racquet, a fishing rod, a golf club, or the like. Tape 38 cooperates with lower loop 33 to close the fingers to form a fist or to wrap around the handle of the sports implement or to grip exercise bars, or the like. Tapes 37 and 38 are threaded through their respective loops 32 and 33 and doubled back upon themselves to be fastened snugly at whatever location provides the desirable tightness of grip. The preferred fastener for both tapes 37 and 38 is a "Velcro" fastener. Tape 37 has one end affixed at juncture 23 and has patches of fabric hooks and fabric loops attached to the side facing mitten section face 20. In order to show this feature tape 37 has been twisted as at 50 to show patches 39 and 40 which are fabric loops and fabric hooks, respectively. It is, of course, entirely operable to reverse these patches. Similarly, tape 38 is affixed to the glove at the top edge 26 of mitten section 20 and is threaded through loop 33 and doubled back upon itself for fastening with "Velcro" fasteners. The back side of tape 38, i.e., the side facing the same direction as back side 25 of palm and wrist section 21, is covered completely with fabric loops. When tape 38 is pulled through loop 33 to form a reasonably tight grip or fist, top edge 26 of mitten section 20 is close to lower loop 33. This requires fabric loops on tape 38 to cooperate with fabric hooks on pad 51 which covers most of the back side of mitten section 20 (see FIG. 2). Pad 51 also serves to stiffen the back of mitten section 20. It is, however, entirely operable to reverse the positions of fabric loops and fabric hooks, i.e., for the back side of tape 38 to be covered with fabric hooks and pad 51 to be fabric loops, with regard to releasably fastening same.

The third tunnel loop 34 is positioned on back side 25 of palm and wrist section 21 on strip 35 and positioned vertically so as not to interfere with the fastening of straps 29, 30, and 31 to strip 35. That position can be found between straps 29 and 31 (as shown in FIG. 2) or between straps 29 and 30. Tunnel loop 34 cooperates with tape 38 which is threaded through loop 34 and doubled back upon itself and fastened by "Velcro" fasteners. Shown on FIG. 1 are two patches 42 and 43 of fabric hooks and fabric loops on the front side of tape 38 which are used to fasten tape 38 to itself after being threaded through loop 34.

It may be important to support the wrist and hand to prevent any forward or backward flexure or bending, such as found in bowler's gloves with removable wrist supports as shown in U.S. Pat. No. 4,138,108 to C.H. Robinson and U.S. Pat. No. 4,190,906 to E.E. Patton, Jr. Palm and wrist section 21 includes a pocket 44 on front side 24 and a pocket 45 on back side 25 to receive supports 46 and 47, respectively, (see FIGS. 3-6). Each of pockets 44 or 45 is completely enclosed except for an opening 57 or 58 into which supports 46 or 47 may be inserted. Supports 46 and 47 are thin strips of stiff material, such as aluminum, steel, plastic, etc., shaped to fit the part of the hand and wrist to be supported. Support 46 has a convex portion 48 to fit over the heel of the palm and extend upward to the center of the palm. Support 47 is flat to fit the contour of the wrist and back of the hand when fully extended in a straight alignment. A cut out portion 49 is designed to permit the wristbone protruding from the outside of the wrist not to be contacted or made uncomfortable by undue pressure from support 47. It is to be understood that the glove of this invention may be used without either of supports 46 and 47 being inserted into pockets 44 and 45, or either of supports 44 and 45 may be used without the other.

Figure 11:
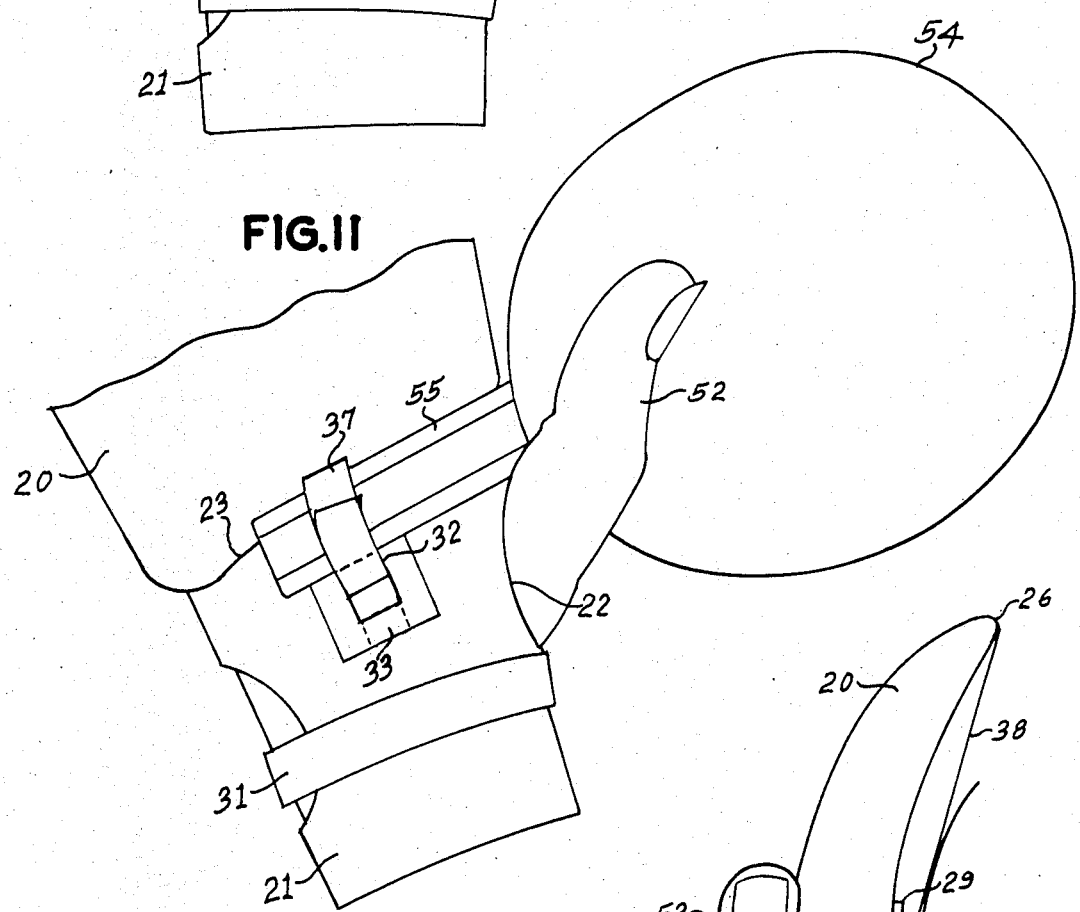
FIG. 11 is a schematic illustration of one of the embodiments of the gloves of this invention around a hand holding a ping pong paddle.
Figure 12:
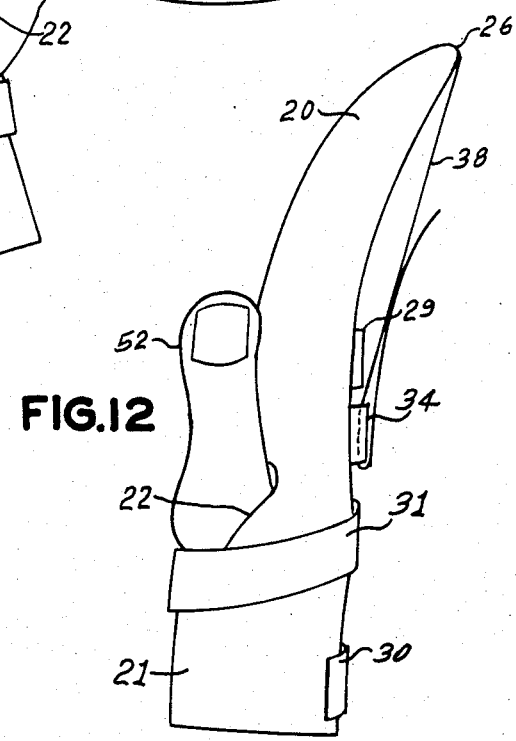
FIG. 12 is a schematic illustration of one of the embodiments of the gloves of this invention around a hand and employed to fully extend the fingers and stretch them slightly backward.

In FIGS. 7-12 there are shown various ways in which the glove of this invention may be employed. In FIGS. 7 and 12, there is shown an embodiment of a glove employing tunnel loop 34 and tape 38 to exercise the hand and fingers of a patient whose fingers tend to curl into a fist in their normal relaxed condition. This frequently occurs with patients who have suffered from a stroke or from arthritis. Therapy for such patients may involve stretching and holding the fingers in an open extended position, and even bent backwards to some degree. Such a position is shown in FIG. 7 with no hand in the glove, and in FIG. 12 with a hand in the glove. It can be seen that by threading tape 38 through tunnel loop 34 and then doubling the free end of tape 38 back upon itself, the cooperating fabric hooks and fabric loops on the front side of tape 38 are fastened to hold mitten section 20 and the fingers inside in any degree of stretching backward that can be reached. Such a glove as shown in FIGS. 7 and 12 need not include any other tunnel loops (such as 32 and 33) nor tape 37, nor pad 51, nor the fabric loops 41 on the back side of tape 38.

In FIGS. 8, 9, and 11 there is shown the embodiment of the glove used for gripping and holding a sports implement, e.g., a ping pong paddle as shown in FIG. 11. In this embodiment the glove requires the use of tunnel loops 32 and 33 along with tapes 37 and 38. In the first operation, the ping pong paddle 54 is positioned with its handle 55 across the palm and hooked by thumb 52 in its normal position. Tape 37 is then threaded through upper tunnel loop 32 and pulled tightly enough to hold handle 55 firmly. The free end of tape 37 is then doubled back upon itself to fasten it in place by means of the "Velcro" fastener patches 39 and 40 of FIG. 1. The next step is to tighten mitten section 20 around handle 55 to provide the gripping action of the fingers. This is accomplished by threading tape 38 through lower tunnel loop 33, pulling it tight, and doubling the free end of tape 38 back upon itself to fasten the fabric loops on the back side of tape 38 to the fabric hooks on pad 51 on the back side of mitten section 20. This is similar to the position shown in FIG. 10. Partially tightened gloves are shown in two views in FIGS. 8 and 9, without the hand being shown, to illustrate how the glove is made to grip a sports implement.

FIG. 10 illustrates how an embodiment of a glove may be used to wrap a hand around a horizontal bar or other similar component of an exercise device, such as weights, oars of a rowing machine, vertical bars of an exercise machine, or the like. In this embodiment, it may be convenient to employ a glove having only lower tunnel loop 33 and tape 38, not including loops 32 and 34 and their cooperating tapes 37 and the front side of tape 38. In this use the hand in the glove is merely wrapped around horizontal bar 53 with thumb 53 on one side of bar 53 and the hand and glove on the other side of bar 53. Tape 38 is then threaded through loop 33, pulled tight, and the free end of tape 38 is doubled back on strip 51 to be tightly fastened by the components of a "Velcro" fastener. It is to be understood that the glove of FIGS. 8, 9, and 11 could also be used to this purpose by fastening tape 37 around horizontal bar 53 and threading it through loop 32 as described above, with respect to the ping pong paddle 54.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

We claim:

1. A glove for use by a handicapped person during therapeutic exercise, the glove comprising a mitten section to enclose four fingers of the wearer attached to a palm and wrist section to wrap around the palm and wrist of the wearer, said palm and wrist section having a front side, a back side, and an opening for the thumb of the wearer to extend outward; said palm and wrist section being adjustably tightenable to the hand and wrist of the wearer by a plurality of straps attached thereto adapted to wrap around and fasten to said back side by means of a fastener employing cooperating fabric loops and fabric hooks, an elongated tape having a free end and a fixed end, the fixed end attached to the middle of the top edge of said mitten section, a tape engaging eye attached to said palm and wrist section, said tape adapted to be threaded through said eye and doubled back upon itself to be fastened at any selected position by means employing fabric loops and fabric hooks.

2. The glove of claim 1 wherein said eye is on said front side.

3. The glove of claim 2 which additionally includes a second eye on said front side spaced between said eye and said mitten section, and a second tape attached at one end thereof to the juncture between said mitten section and said front side, with the free end of said second tape adapted to be threaded through said second eye and doubled back upon itself and be fastenable to itself by means of cooperating fabric hooks and fabric loops.

4. The glove of claim 1 wherein said eye is on said back side.

5. The glove of claim 1 wherein said palm and wrist section includes two lengthwise pockets, one on said front side and one on said back side and two thin stiff strips insertable respectively into each said pocket and adapted to maintain the hand and wrist of said wearer in a substantially inflexible position.

6. The glove of claim 1 which additionally comprises a third eye on said back side and adapted to be engaged by said tape being threaded therethrough and doubled back upon itself and fastened to itself by means employing fabric hooks and fabric loops.

7. The glove of claim 1 wherein said eye is a tunnel loop of the material of said palm and wrist section.

8. The glove of claim 1 wherein said eye is a D-ring.

9. An integral flexible glove for use in therapeutic exercise of the hand, which comprises a mitten section adapted to enclose the four fingers of a hand and a palm and wrist section adapted to cover the palm, the back of the hand, and the wrist with an opening for the thumb to extend freely outward of said glove, said palm and wrist section having a palm side and a back side joined together around the thumb side thereof and having a lengthwise opening along the little finger side thereof, a plurality of elongated straps extending laterally outward from said lengthwise opening and adapted to wrap around to said back side where each said strap and said back side are releasably fastenable to each other by means of fabric hooks and fabric loops, a pair of longitudinally spaced tunnel loops on said palm side, including an upper loop adjacent the juncture of said palm and wrist section and said mitten section and a lower loop adjacent the heel of the palm of the wearer, a first elongated tape with one end thereof attached to said palm side adjacent the juncture of said mitten section and said palm and wrist section and having a free end adapted to be threaded through said upper loop and doubled back upon itself and fastenable thereto by means including fabric hooks and fabric loops, and a second elongated tape with one end attached to the top edge of said mitten section and having a free end adapted to be threaded through said lower loop and doubled back upon itself and fastenable thereto by means including fabric hooks and fabric loops.

10. The glove of claim 9 which additionally comprises a lengthwise first pocket medially of said palm side and a stiff support strip insertable into said first pocket and having a curved contour substantially similar to that from mid-palm to wrist of a normal hand and arm, and a lengthwise second pocket medially of said back side and a stiff support strip insertable into said second pocket and having a substantially planar contour to maintain the back of the hand and the wrist in straight alignment.

11. An integral flexible glove for use in therapeutic exercise of the hand, which comprises a mitten section adapted to enclose the four fingers of a hand and a palm and wrist section adapted to cover the palm, the back of the hand, and the wrist with an opening for the thumb to extend freely outward of said glove, said palm and wrist section having a palm side and a back side joined together around the thumb side thereof and having a lengthwise opening along the little finger side thereof, a plurality of elongated straps extending laterally outward from said lengthwise opening and adapted to wrap around to said back side where each said strap and said back side are releasably fastenable to each other by means of fabric hooks and fabric loops, a tunnel loop generally in the middle of said back side and an elongated tape with one end attached to the top edge of said mitten section and having a free end adapted to be threaded through said loop and doubled back upon itself and fastenable thereto by means including fabric hooks and fabric loops.

12. The glove of claim 11 which additionally comprises a lengthwise first pocket medially of said palm side and a stiff support strip insertable into said first pocket and having a curved contour substantially similar to that from mid-palm to wrist of a normal hand and arm, and a lengthwise second pocket medially of said back side and a stiff support strip insertable into said second pocket and having a substantially planar contour to maintain the back of the hand and the wrist in straight alignment.

13. An integral flexible glove for use in therapeutic exercise of the hand, which comprises a mitten section adapted to enclose the four fingers of a hand and a palm and wrist section adapted to cover the palm, the back of the hand, and the wrist with an opening for the thumb to extend freely outward of said glove, said palm and wrist section having a palm side and a back side joined together around the thumb side thereof and having a lengthwise opening along the little finger side thereof, a plurality of elongated straps extending laterally outward from said lengthwise opening and adapted to wrap around to said back side where each said strap and said back side are releasably fastenable to each other by means of fabric hooks and fabric loops, a tunnel loop generally in the middle of said front side adjacent the heel of the palm of the wearer and an elongated tape with one end attached to the top edge of said mitten section and having a free end adapted to be threaded through said loop and doubled back upon itself and fastenable thereto by means including fabric hooks and fabric loops.

14. The glove of claim 13 which additionally comprises a lengthwise first pocket medially of said palm side and a stiff support strip insertable into said first pocket and having a curved contour substantially similar to that from mid-palm to wrist of a normal hand and arm, and a lengthwise second pocket medially of said back side and a stiff support strip insertable into said second pocket and having a substantially planar contour to maintain the back of the hand and the wrist in straight alignment.

15. An integral flexible glove for use in therapeutic exervice of the hand, which comprises a mitten section adapted to enclose the four fingers of a hand and a palm and wrist section adapted to cover the palm, the back of the hand, and the wrist with an opening for the thumb to extend freely outward of said glove, said palm and wrist section having a palm side and a back side joined together around the thumb side thereof and having a lengthwise opening along the little finger side thereof, a plurality of elongated straps extending laterally outward from said lengthwise opening and adapted to wrap around to said back side where each said strap and said back side are releasably fastenable to each other by means of fabric hooks and fabric loops, a pair of longitudinally spaced tunnel loops on said palm side, including an upper loop adjacent the juncture of said palm and wrist section and said mitten section and a lower loop adjacent the heel of the palm of the wearer, a first elongated tape with one end thereof attached to said palm side adjacent the juncture of said mitten section and said palm and wrist section and having a free end adapted to be threaded through said upper loop and doubled back upon itself and fastenable thereto by means including fabric hooks and fabric loops, a second elongated tape with one end attached to the top edge of said mitten section and having a free end adapted to be threaded through said lower loop and doubled back upon itself and fastenable thereto by means including fabric hooks and fabric loops, and a third tunnel loop generally in the middle of said back side with said second elongated tape adapted to be threaded therethrough and doubled back upon itself and fastenable thereto by means including fabric hooks and fabric loops.

16. The glove of claim 15 which additionally comprises a lengthwise first pocket medially of said palm side and a stiff support strip insertable into said first pocket and having a curved contour substantially similar to that from mid-palm to wrist of a normal hand and arm, and a lengthwise second pocket medially of said back side and a stiff support strip insertable into said second pocket and having a substantially planar contour to maintain the back of the hand and the wrist in straight alignment.

* * * * *